United States Patent
Shachar et al.

(10) Patent No.: US 11,540,775 B2
(45) Date of Patent: *Jan. 3, 2023

(54) OPTICALLY COUPLED CATHETER AND METHOD OF USING THE SAME

(71) Applicant: Neurokinesis Corp., Los Angeles, CA (US)

(72) Inventors: Josh Shachar, Santa Monica, CA (US); Marc Rocklinger, Marina del Rey, CA (US); Eli Gang, Los Angeles, CA (US)

(73) Assignee: Neuro-Kinesis Inc., Los Angeles, CA (US)

( * ) Notice: Subject to any disclaimer, the term of this patent is extended or adjusted under 35 U.S.C. 154(b) by 859 days.

This patent is subject to a terminal disclaimer.

(21) Appl. No.: 16/424,202

(22) Filed: May 28, 2019

(65) Prior Publication Data

US 2020/0375541 A1 Dec. 3, 2020

(51) Int. Cl.
| | |
|---|---|
| *A61B 5/00* | (2006.01) |
| *A61B 5/24* | (2021.01) |
| *A61B 5/302* | (2021.01) |
| *A61M 25/01* | (2006.01) |

(52) U.S. Cl.
CPC .......... *A61B 5/6852* (2013.01); *A61B 5/0017* (2013.01); *A61B 5/0084* (2013.01); *A61B 5/2415* (2021.01); *A61B 5/302* (2021.01); *A61B 5/7435* (2013.01); *A61M 2025/0166* (2013.01)

(58) Field of Classification Search
None
See application file for complete search history.

(56) References Cited

U.S. PATENT DOCUMENTS

| | | | |
|---|---|---|---|
| 6,575,965 B1 * | 6/2003 | Fitch .................. | A61B 17/1214 606/15 |
| 6,898,464 B2 * | 5/2005 | Edell .................... | A61B 5/0017 128/903 |
| 7,865,246 B2 * | 1/2011 | Forsberg .............. | A61N 1/0551 607/2 |

(Continued)

FOREIGN PATENT DOCUMENTS

WO WO-2022046425 A1 * 3/2022

*Primary Examiner* — Carl H Layno
*Assistant Examiner* — Manolis Pahakis
(74) *Attorney, Agent, or Firm* — Marcus C. Dawes; Daniel L. Dawes

(57) ABSTRACT

The embodiments include an apparatus used in combination with a computer for sensing biopotentials. The apparatus includes a catheter in which there is a plurality of sensing electrodes, a corresponding plurality of local amplifiers, each coupled to one of the plurality of sensing electrodes, a data, control and power circuit coupled to the plurality of local amplifiers, and a photonic device bidirectionally communicating an electrical signal with the data, control and power circuit. An optical fiber optically communicated with the photonic device. The photonic device bidirectionally communicates an optical signal with the optical fiber. An optical interface device provides optical power to the optical fiber and thence to the photonic device and receives optical signals through the optical fiber from the photonic device. The optical interface device bidirectionally communicates an electrical data, control and power signal to the computer.

15 Claims, 12 Drawing Sheets

(56) References Cited

U.S. PATENT DOCUMENTS

| | | | | |
|---|---|---|---|---|
| 8,139,225 B2* | 3/2012 | Zhang | ............... | A61B 5/0002 |
| | | | | 356/477 |
| 9,381,063 B2* | 7/2016 | Gang | ............... | A61B 34/73 |
| 9,414,940 B2* | 8/2016 | Stein | ............... | A61F 2/4657 |
| 9,937,062 B2* | 4/2018 | Stein | ............... | A61F 2/4657 |
| 10,699,559 B2* | 6/2020 | Van Der Mark | ...... | G08C 23/04 |
| 2002/0107557 A1* | 8/2002 | Edell | ............... | A61B 5/0017 |
| | | | | 607/60 |
| 2010/0160737 A1* | 6/2010 | Shachar | ............... | A61B 17/02 |
| | | | | 600/202 |
| 2012/0078278 A1* | 3/2012 | Bales, Jr. | ....... | A61B 17/320092 |
| | | | | 307/116 |
| 2012/0197094 A1* | 8/2012 | Zhang | ............... | A61B 6/04 |
| | | | | 600/300 |
| 2012/0232430 A1* | 9/2012 | Boissy | ............... | A61B 5/1118 |
| | | | | 600/595 |
| 2014/0018792 A1* | 1/2014 | Gang | ............... | A61B 18/1492 |
| | | | | 606/41 |
| 2015/0157354 A1* | 6/2015 | Bales, Jr. | ............... | A61B 50/20 |
| | | | | 606/169 |
| 2015/0313501 A1* | 11/2015 | Shachar | ............... | A61B 5/302 |
| | | | | 600/374 |
| 2015/0335231 A1* | 11/2015 | Van Der Mark | ...... | A61B 5/318 |
| | | | | 600/407 |
| 2019/0201695 A1* | 7/2019 | Hsu | ............... | A61N 1/36075 |

\* cited by examiner

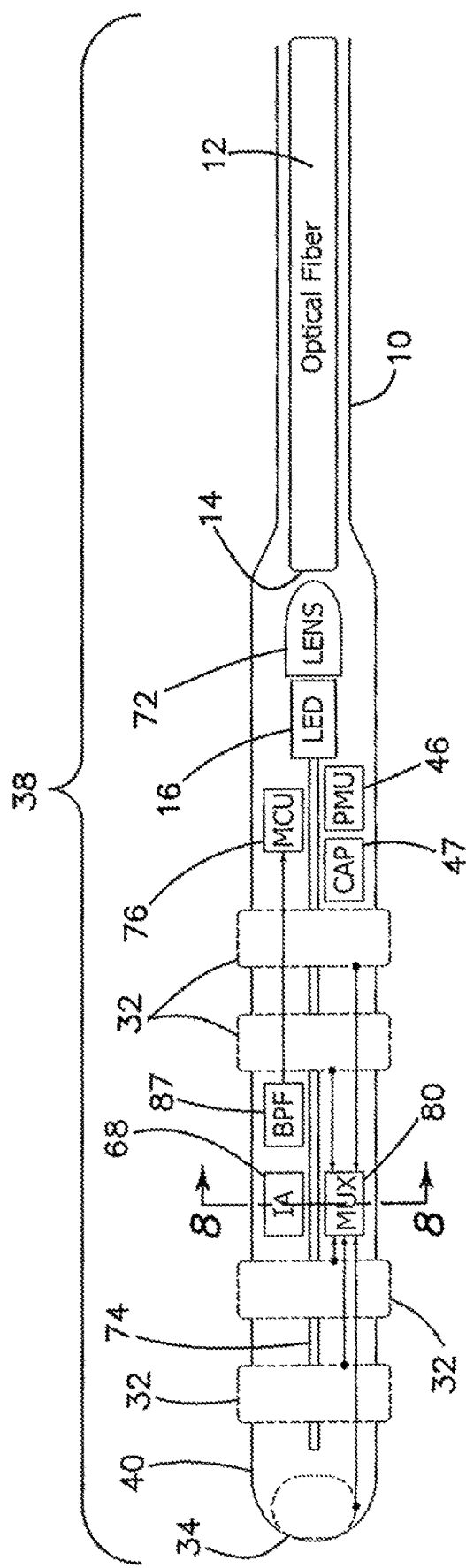
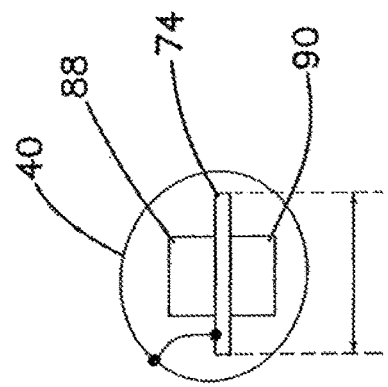
FIG. 7
FIG. 8

OPTICALLY COUPLED CATHETER AND METHOD OF USING THE SAME

BACKGROUND

Field of the Technology

The invention relates to the field of bioelectric catheters and in particular to catheters having MOSFET sensor arrays using a local amplifier, such as appear in CPC subclasses: G01N 27/4145; G01N 27/4146; G01N 33/5438; H01L 51/0049; and H01L 51/0558.

Description of the Prior Art

In a conventional diagnostic catheter, the weak biopotential signals picked up by the right electrodes in the distal tip are amplified in external equipment that is separated from the electrodes by several meters of wiring. This wiring is vulnerable to noise pickup from 60 Hz power mains and higher frequency interference from operating room equipment. As a result, signals such as complex fractionated atrial electrograms with amplitudes in the 10's of µVpp are often buried in the noise.

Existing intracardiac recording techniques, while they have served the clinician and basic scientists reasonably well over the past three to four decades, suffer from several inherent limitations. By the very nature of utilizing electrodes connected by long cables to a distant differential amplifier, these systems are subject to line "noise," ambient EMI, cable motion artifacts, and faulty connections.

Local signals are subject to recording of far-field signals, which at times render the interpretation of complex, rapid arrhythmias very difficult, if not impossible.

The conflation of far-field and signals of real interest, such as pulmonary vein fiber potentials, accessory pathway signals, and slow pathway potentials, can sometimes be the cause of failed ablations. The ability to record local electric activity with great precision and to the exclusion of far-field signals would be of paramount importance.

Current recording systems frequently cannot differentiate low-amplitude, high-frequency signals from background noise. Extremely low-amplitude signals, such as those generated during slow conduction within a myocardial scar, are frequently missed or lost in the background noise when amplifier gain is made sufficiently high to attempt to record such signals.

Continuous, low amplitude, fractionated high-frequency signals such as those frequently seen in the atria of patients with chronic atrial fibrillation, cannot be further characterized using existing recording technologies. These signals may contain important biologic and electrophysiologic information. For example, these signals may represent important areas of scarring that are responsible for formation of rotors. Alternatively, they may be manifesting discharges from contiguous epicardial parasympathetic ganglionated plexi.

In one application, such as in Renal Denervation, variabilities in human microanatomy of renal nerve distribution and density of nerve endings from patient to patient mean that we cannot take a "cookie cutter" approach to circumferential ablation sites. Variability in neuron function in type and size, from large to small means that we cannot only ablate the larger regular-discharging neuron sites but must also target the smaller irregular-discharging and non-spontaneous neurons that are tonal and can drive signaling even when the large sites have been successfully ablated.

Mapping of the renal artery allows for a precise identification of renal nerve location and size. Location data can be used to identify precisely where to ablate, while size information can be used to discern neuron types (regular, irregular, and non-spontaneous). This can lead to greater efficacy and a reduced need for serial ablations if the first is ineffective.

Another such application is in electrophysiological studies for identifying different types of arrythmia. Electrophysiology studies are performed by measuring small signals from electrodes placed in the patient's heart in a sometimes very noisy environment. As currently practiced, signal detection in the electrophysiological Lab is subject to external noise from pick-up during the travel of the signal from the catheter tip to the amplifier located several feet away. Signal processing at the multichannel recorder can subject small signals of interest to degradation when appropriately amplified, such that important microvolt-sized signals are lost when noise is filtered out.

Fractionation potentials recorded in scarred myocardial tissue, which serve as ablation targets, as well as pulmonary vein potentials and accessory pathway potentials, need to be accurately characterized.

Barbara Hubbard, in the text "The World According to Wavelets", expresses the fundamental problem of filtering as a method for smoothing the wave characteristics employing lowpass and high pass filtering, and the obvious problem of separating the noise component from the native signal, which is the inability of the system to identify which is which. If we know that a signal is smooth, i.e. changing slowly, and that the noise is fluctuating rapidly, we can filter out noise by averaging adjacent data to eliminate fluctuations while preserving the trend. Noise can also be reduced by filtering out high frequencies. For smooth signals, which change relatively slowly and therefore are mostly lower frequency, this will not blur the signal too much. Many interesting signals are not smooth; they contain high-frequency peaks. Eliminating all high frequencies mutilates the message, "cutting the daisies along with the weeds," in the words of Victor Wicker Hauser of Washington University in St. Louis, adequately expresses the main drawback of post-processing such signals.

BRIEF SUMMARY

The illustrated embodiments of the invention include an apparatus used in combination with a computer for sensing, biopotentials. The apparatus includes a catheter in which there is a plurality of sensing electrodes, a corresponding plurality of local amplifiers, each coupled to one of the plurality of sensing electrodes, a data, control and power circuit coupled to the plurality of local amplifiers, and a photonic device bidirectionally communicating an electrical signal with the data, control and power circuit. An optical fiber optically communicated with the photonic device. The photonic device bidirectionally communicates an optical signal with the optical fiber. An optical interface device provides optical power to the optical fiber and thence to the photonic device and receives optical signals through the optical fiber from the photonic device. The optical interface device bidirectionally communicates an electrical data, control and power signal to the computer.

The optical interface device includes a laser to provide optical power to the optical fiber.

The optical interface device includes a photodetector to receive optical signals through the optical fiber from the photonic device.

The optical interface device includes a digital signal processor to control and communicate with the laser and photodiode, and to communicate with the computer.

The apparatus further includes a catheter cable coupling the optical interface device and the catheter, where the optical fiber is included in the catheter cable, which is MRI compatible and EMI impervious, Only optical signals are communicated within the catheter cable.

The plurality of electrodes each comprise a MOSFET electrode.

The apparatus further includes in one fabricated embodiment a flexible printed circuit board and where the local amplifiers and data, control and power circuit comprise application specific integrated circuits (ASICs) mounted on both sides of the flexible printed circuit board within the catheter having a size of 11 French or smaller.

In other words, the apparatus further includes a flexible printed circuit board and where the local amplifiers and data, control and power circuit comprise application specific integrated circuits (ASICs) mounted on both sides of the flexible printed circuit board having a width of 2.5 mm or less and a height including the ASICs of 2 mm or less.

The photonic device selectively operates as both a light emitting diode or a photodiode depending on bias control.

The data, control and power circuit include a multiplexer communicated to the plurality of electrodes.

The plurality of local amplifiers each have programmable gain.

The plurality of electrodes senses analog electrical biopotentials and the data control and power circuit include an analog to digital converter to process the electrical biopotentials in digital form and the photonic device communicates the electrical digital bipotential through the optical fiber to the optical interface as optical digital biopotential signals.

The catheter is configured as an electrophysiology catheter, renal denervation catheter, neuromodulation catheter, or an epileptic brain catheter.

The apparatus further includes a temperature sensor communicated to the data, control and power circuit.

The illustrated embodiments can also be characterized as a method for sensing biopotentials including the steps of: providing a catheter comprising a plurality of sensing electrodes, a corresponding plurality of local amplifiers, each coupled to one of the plurality of sensing electrodes, a data, control and power circuit coupled to the plurality of local amplifiers; and a photonic device; sensing the biopotentials with the plurality of sensing electrodes; bidirectionally communicating the biopotentials with the data, control and power circuit, providing an optical fiber in a catheter cable optically communicated with the photonic device; bidirectionally communicating an optical signal through the optical fiber; and catheter; providing optical power to the optical fiber and thence to the photonic device; receiving optical signals through the optical fiber from the photonic device; and bidirectionally communicating an electrical data, control and power signal to the computer, so that the catheter cable is MRI compatible and EMI impervious.

The step of sensing the biopotentials with the plurality of sensing electrodes includes the step of sensing the biopotentials with a plurality of locally amplified MOSFET electrodes.

The step of providing a catheter comprising a plurality of sensing electrodes, a corresponding plurality of local amplifiers, each coupled to one of the plurality of sensing electrodes, a data, control and power circuit coupled to the plurality of local amplifiers and a photonic device includes the step of providing a flexible printed circuit board and mounting the local amplifiers and data, control and power circuit in the form of application specific integrated circuits (ASICs) mounted on both sides of the flexible printed circuit board within the catheter having a size of 11 French or smaller, or in the alternative mounted on both sides of the flexible printed circuit board having a width of 2.5 mm or less and a height including the ASICs of 2 mm or less.

The optically coupled catheter of the illustrated embodiments can be used in any field of medical diagnosis or therapy and in particular has specific application to electrophysiology, renal denervation, neuromodulation, nerve-ending measurements in the central nervous system (CNS), and for psychiatric therapy of patients with deep depression or manic depressive state where medicating agents are not effective. A special case is the use of such sensing modality in epileptic seizure, where the electrodes with such resolutions can augment the resolution of the focal point insertion of neuromodulating implantable electrodes where electrical potential at the site averts the epileptic event prior to its occurrence.

The illustrated embodiment is an optical catheter system which is scanner and magnetic resonance imaging (MRI) compatible. It is characterized by a highly flexible catheter without the use of an any shielded wires in the catheter cable. The catheter system is totally immune to any radio frequency (RF) or electromagnetic noise or interference.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 7 is a schematic of the fabrication of the circuitry of FIG. 6 into another embodiment of the flexible catheter, FIG. 8 is a cross sectional view of the catheter of FIG. 7 as seen through section lines 8-8 of FIG. 7.

FIG. 10b is a perpendicular cross-sectional view of the renal artery of FIG. 10a.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
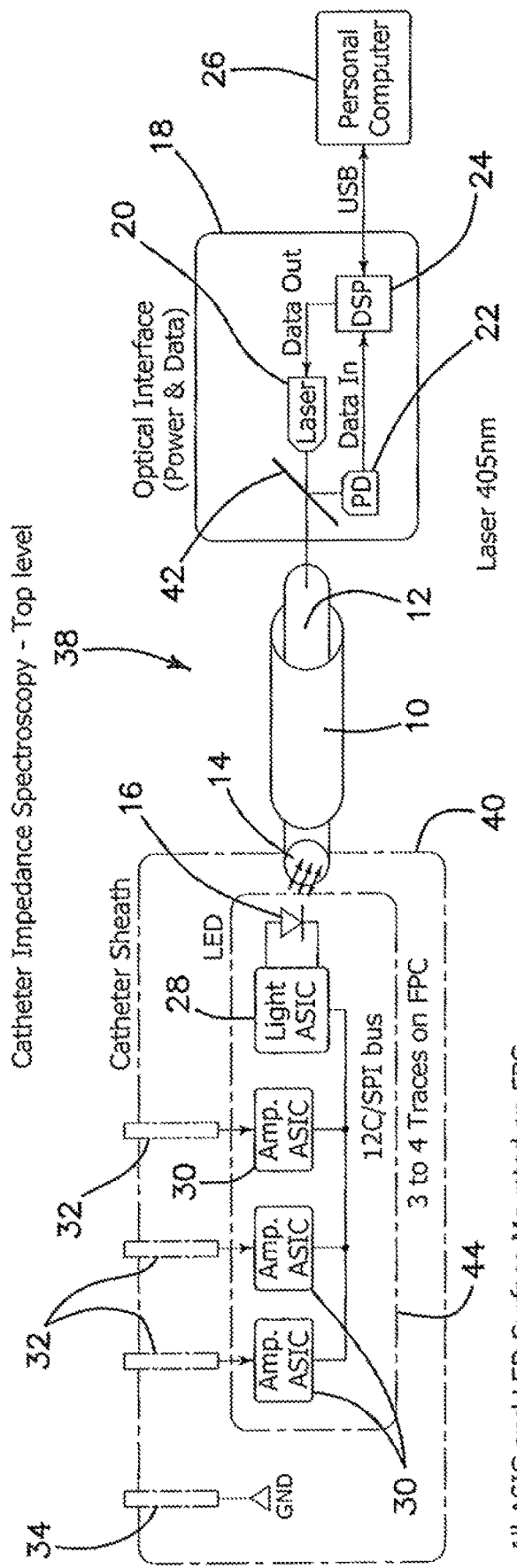
FIG. 1 is a block diagram of an apparatus used in catheter impedance spectroscopy according to the illustrated embodiments of the invention.

FIG. 1 is a block diagram of illustrating an impedance catheter system 38 using local amplifiers 30 according to one of the illustrated embodiments of the invention. A catheter 40 is coupled via a catheter cable 10, which includes an optical fiber 12 to an optical interface 18. Cable 12 and optical fiber 12, which may be several meters long, is coupled to optical interface 18, which in turn is coupled to a personal computer 26 or other data processor or control device or system through a conventional universal serial bus (USB). Optical interface 18 provides power to catheter 40 and serves to handle data flow to and from catheter 40. A laser 20 is included in optical interface 18 and is controlled by a digital signal processor (DSP) 24. For example, a 1 W 405 nm Titanium-Sapphire laser or laser diode with about 50 mW to 150 MW optical output may be used. Any electrical control signals from computer 26 are communicated through DSP 24 to laser 20, where they are output as optical or photonic signals, and are coupled into optical fiber 12. Similarly, photonic data on optical fiber 12 input into optical interface 18 is received by photodiode 22 and converted into an electrical data signal communicated to DSP 24 and hence to computer 26. Dichroic mirror 42 diverts a portion of the output of laser 20 to photodiode 22 for feedback control of the laser level.

The transmitted photonic signals from optical interface 18 a communicated through catheter cable 10 to emitting end 14 of optical fiber 12 and are directed into a GaN LED (Philips Lumileds Luxeon Z) or an InGaN/GaN light emitting diode (LED) and photodetector (PD) 16. According to the direction of bias applied to LED/PD 16, it operates either to receive a photonic signal and convert it into an electrical replica when biased as a photodiode or to generate a photonic signal in response to an electrical input when biased as an LED. A semiconductor such as InGaN/GaN with multiple quantum well structure commonly used for light emitting diodes can be employed for dual functions of optoelectronics devices exhibiting photodetector properties in under variable load conditions (bias). The principle of such device is noted by the fact that Optical emission resulting from 405 nm selective photoexcitation of carriers in the GaInN/GaN quantum well (QW) active region of a light-emitting diode, which reveals two recombination channels. The first recombination channel is the recombination of photoexcited carriers in the GaInN QWs. The second recombination channel is formed by carriers that leak out of the GaInN QW active region, which in turn self-bias the device in forward direction, and thereby induce a forward current, and subsequently recombine in the GaInN active region in a spatially distributed manner. The results indicate dynamic carrier transport involving active, confinement, and contact regions of the device. Thus, one can easily integrate photodetectors with LEDs using the same epi-structure to realize a GaN-based optoelectronic integrated circuit (OEIC). See Y. D. Jhou et. al., "Nitride-based light emitting diode and photodetector dual function devices with InGaN/GaN multiple quantum well structures", Solid State Electronics, Vol. 49, No. 8, August 2005, pp 1347-1351. And Martin F. Schubert et al. "Electroluminescence induced by photoluminescence excitation in GaInN/GaN light-emitting diodes" applied physics letter 95,191105, (2009).

LED/PD 16 is coupled to light application specific integrated circuit (ASIC) 28, which signal conditions and communicates a plurality of signals on serial peripheral interface (SPI) bus 44 to a plurality of amplifier ASIC's 30, each of which are coupled to an electrode 32. The plurality of MOSFET electrodes 32 together with tip ground electrode 34 are the sensing points of catheter 40, similar to the MOSFET electrodes described in greater detail in Shachar, et. al., "Apparatus for magnetically deployable catheter with MOSFET sensor and method for mapping and ablation", U.S. Pat. No. 7,869,854 incorporated herein by reference as if set out in its entirety. Sensed biopotentials from MOSFET electrodes 32 are locally amplified by amplifier ASICs 30 and communicated via bus 44 into light ASIC 28 to be multiplexed out to LED/PD 16 and communicated as multiplexed photonic signals on optical fiber 12.

Figure 2:
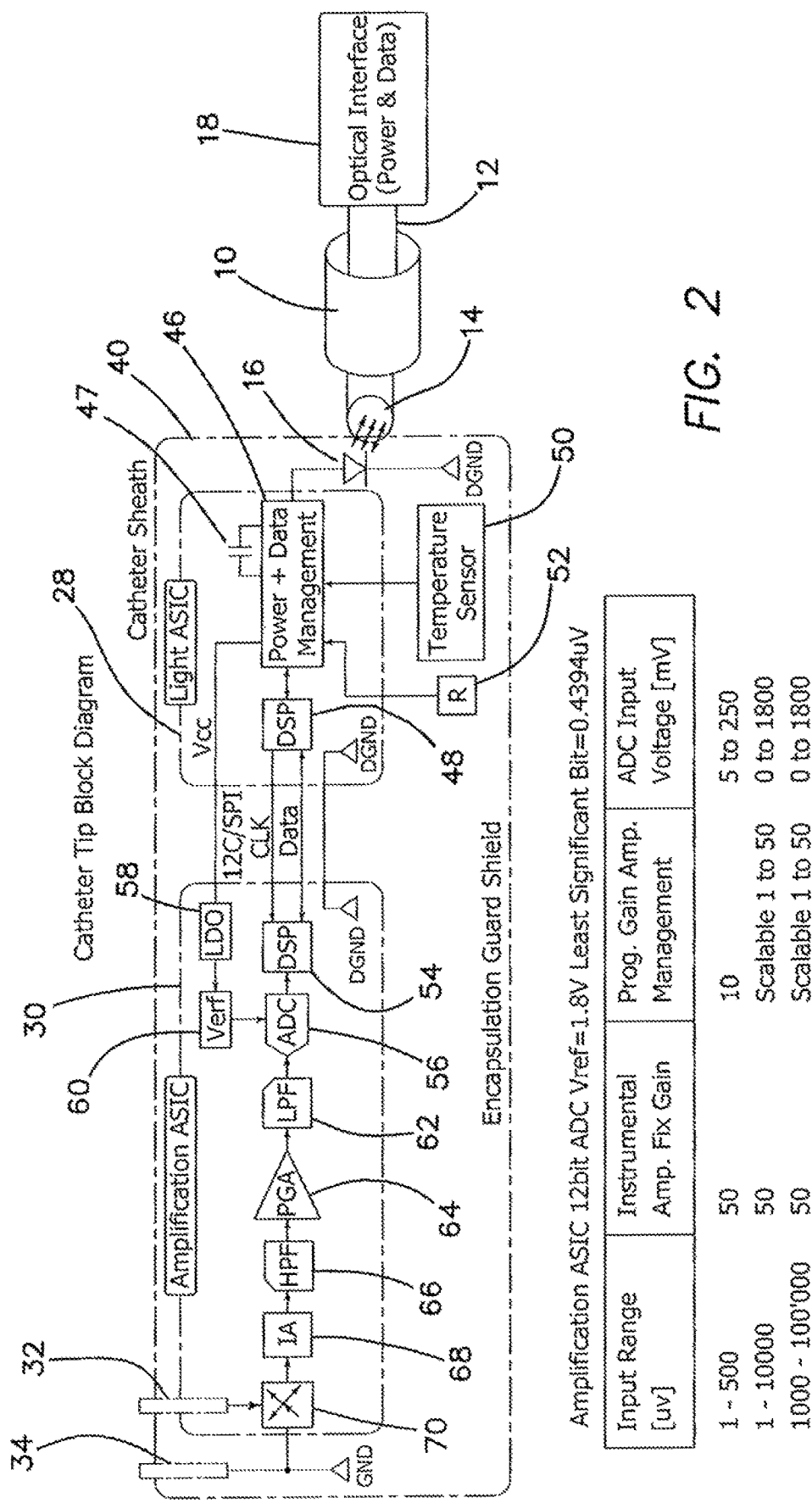
FIG. 2 is a block diagram of the components in the catheter tip of FIG. 1 according to the illustrated embodiments of the invention.

FIG. 2 is a block diagram of the components in the catheter tip of FIG. 1 according to the illustrated embodiments of the invention. Light ASIC 28 includes a power and data module 46, which converts the optical signal originating from laser 20 into both an electrical power signal for catheter 40 as well of control signals and output data signals. Module 46 converts electrical power from LED/PD 16 derived from pulsed light into continuous capacitive stored power stored on capacitor 47, Module 46 is coupled to LED/PD 16 and controls the bias on to LED/PD 16 as well as bidirectionally communicating digital signals thereto and therefrom. Module 46 is coupled to the catheter ground via a coupling resistor 52 used to monitor any leakage current protection and to a temperature sensor 50 by which signal conditioning and compensation are provided for catheter 40.

PMU Module 46 is also bidirectionally coupled to DSP 48 by which a synchronizing clock signal is provided to amplifier ASICs 30 and through with data and control signals are bidirectionally communicated.

Figure 5:
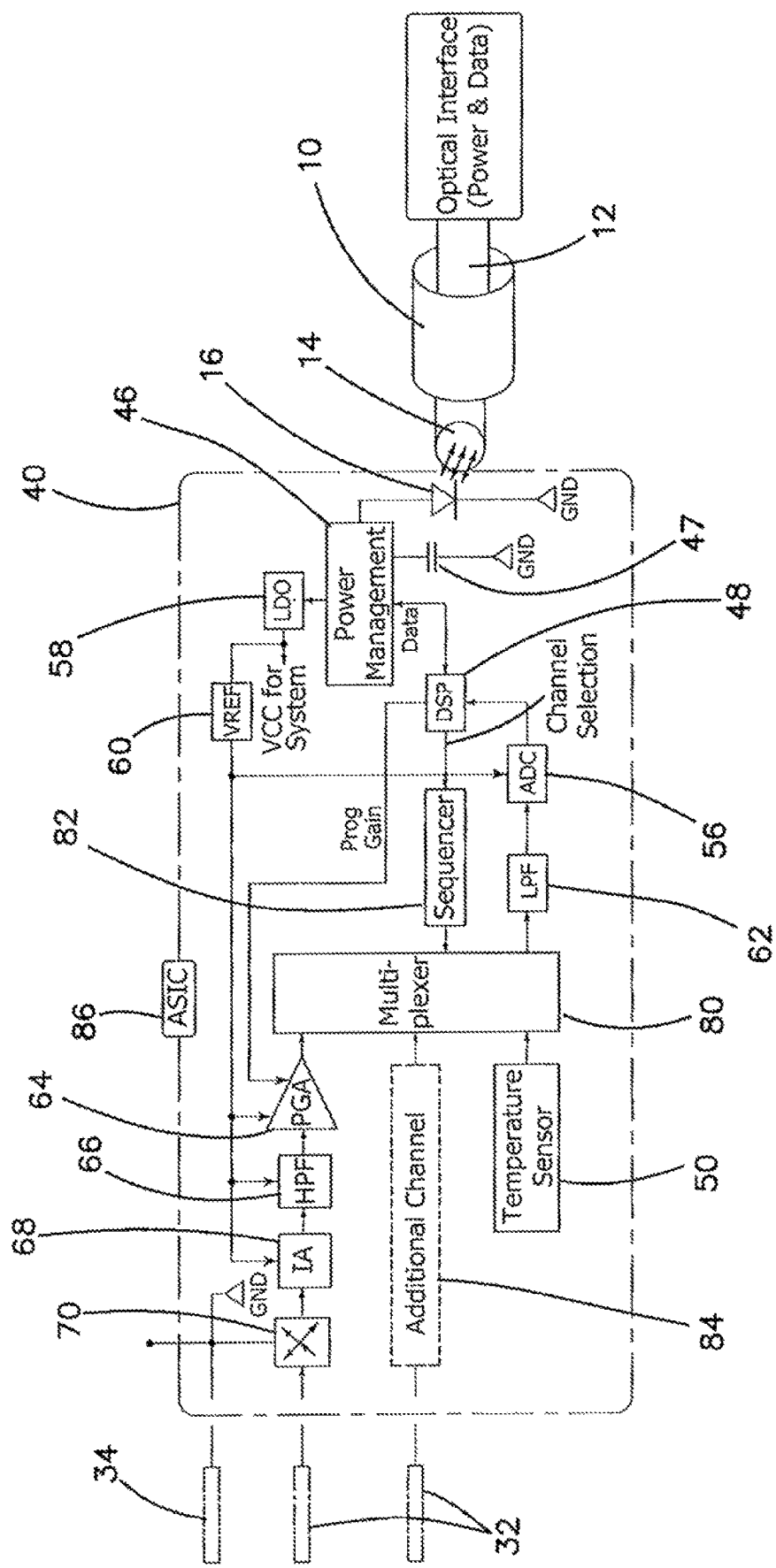
FIG. 5 is a block diagram of another embodiment of the components in the catheter tip of FIG. 1.

DSP 48 communicates with DSP 54 in amplifier ASIC 30, which receives the data signal sensed by electrode 32 through an analog to digital converter (ADC) 56. ADC 56 in turn is powered by module 46 through low dropout (LDO) voltage regulator 58 driving a reference voltage circuit 60 coupled to ADC 56. ADC 56 receives the data signal from low pass filter (LPF) 62 driven by programmable gain amplifier (PGA) 64. PGA 64 takes its input signal from high pass filter (HPF) 66 driven by a fixed gain instrumentation amplifier (IA) 68 (here a Texas Instrument or Analog Devices AD8235ACBZ-P7). Electrode 32 and tip ground electrode 34 are coupled to IA 68 through an electrostatic discharge protection circuit 70. In the illustrated embodiment IA 68 has a fixed gain of 50 while PGA 64 is programmable from 1-50, thus making a 1-500 µV sensed signal at electrode 32 can be programmable and appear as a 5-250 mV input signal to ADC 56, if PGA 64 is given a gain of 10. Similarly, a 1-10,000 µV sensed signal at electrode 32 can be scaled to appear as a 0-1800 mV input signal to ADC 56 by programming PGA 64 with a gain between 1 to 50; or a 1-100,000 µV sensed signal at electrode 32 appears as a 0-1800 mV input signal to ADC 56 by programming PGA 64 with a gain between 1 to 50. In this manner different electrode input signal ranges are programmable and accommodated FIG. 5 is a block diagram of another embodiment of the components in the catheter tip of FIG. 1, similar to the embodiment of FIG. 2. In the embodiment of FIG. 5 light ASIC 28 and amplifier ASIC 30 have been combined into an integrated ASIC 86. In integrated ASIC 86 includes a multiplexer (MUX) 80 coupled to a plurality of electrode channels 84, one of which is shown in detail in FIG. 5. Temperature sensor 50 is also provided as an input to MUX 80. A sequencer circuit 82 is coupled between MUX 80 and DSP 48 bidirectionally coupled to module 46 to control the sequence of channels 84 sampled. A programmable gain control signal is generated by DSP 48 and coupled to PGA 64. Data is provided by PGA 64 for each electrode 32 through MUX 80 to a low pass filter 62 to analog-to-digital converter 56 for communication to DSP 56.

Figure 3:
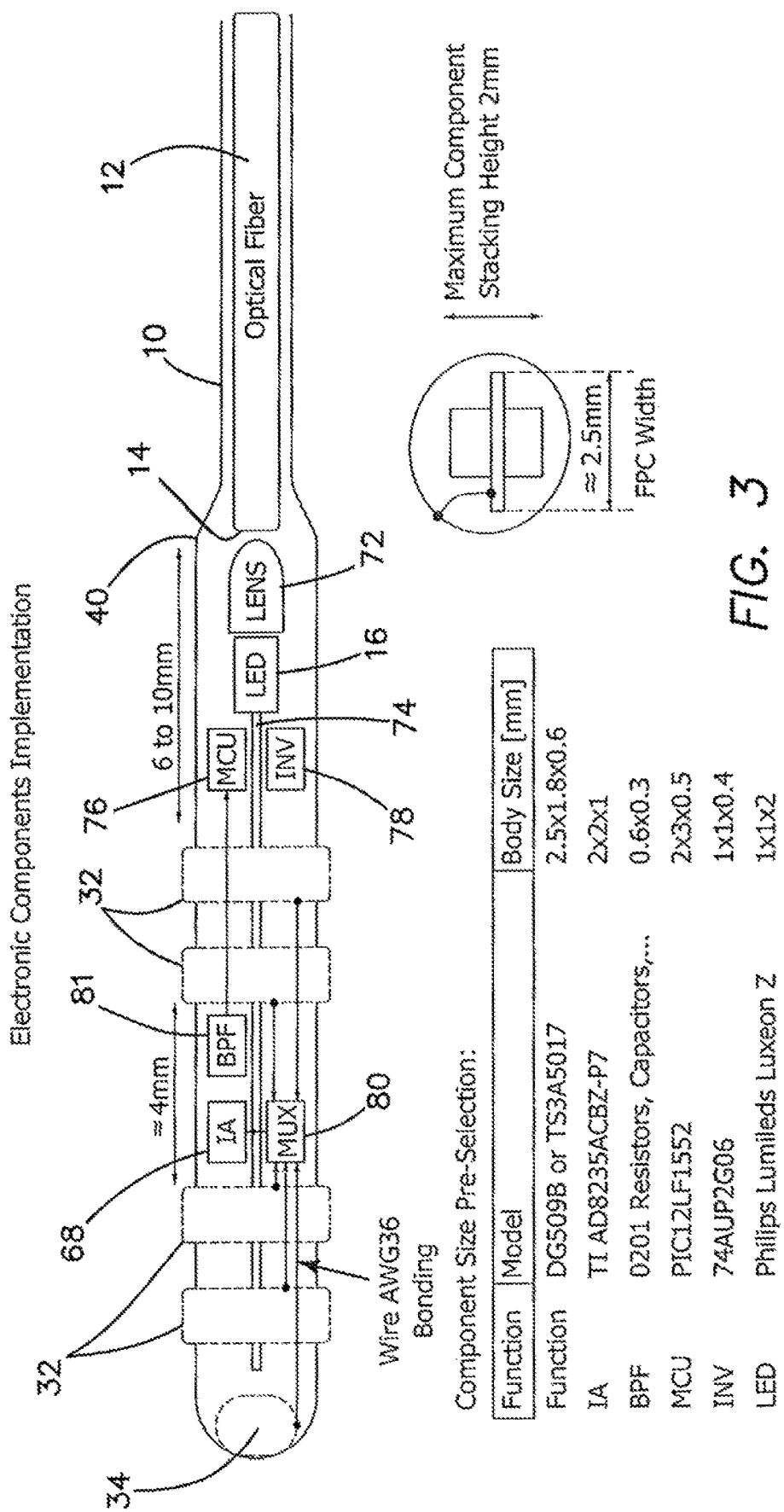
FIG. 3 is a schematic diagram of one embodiment of the fabrication of the components in the catheter tip according to the illustrated embodiments of the invention in which the catheter system is included in a size 11 French catheter or smaller.

FIG. 3 is a schematic diagram illustrating the fabrication of the components in the catheter tip according to the illustrated embodiments of the invention in which the catheter system is included in a size 11 French catheter or smaller. Optical fiber 12 in catheter cable 10 is coupled through end 14 to an aspherical lens 72 directing collimated light from optical fiber 12 into LED/DP 16. LED/DP 16 is disposed adjacent to the proximate end of flexible printed circuit board (FPCB) 74 which extends through the body of catheter sheath 40. In the embodiment of FIG. 3 a microcontroller (MCU) 76 with a built-in analog-to-digital converter is disposed on one side of FPCB 74 and an inverting amplifier circuit (INV) 78 is disposed on the opposing side of the FPCB 74. INV 78 (here a Diodes 74AUP2G06) is a low-power dual inverter with open-drain output. It provides two inverting buffers with open-drain output. The output of the device is an open drain and can be connected to other open-drain outputs to implement active-LOW wired-OR or active-HIGH wired-AND functions. A Schmitt-trigger action at all inputs makes the circuit tolerant to slower input rise and fall times across the entire VCC range from 0.8 V to 3.6 V. INV 78 ensures a very low static and dynamic power consumption across the entire VCC range from 0.8 V to 3.6 V. It is fully specified for partial power-down applications using IOFF. The IOFF circuitry disables the output, preventing the damaging backflow current through the device when it is powered down. The stacked height of MCU 76, INV 78 and FPCB 74 is about 2 mm and the width of FPCB 74 is about 2.5 mm, the width of MCU 76 and INV 78 being less. Also coupled to MCU 76 on FPCB 74 is a bandpass filter 81 and thence to IA 68. Disposed on the opposing side of FPCB 74 from IA 68 is a multiplexer (MUX) 80. MUX 80 is coupled to the plurality of MOSFET electrodes 32 on catheter 40 and to tip ground electrode 34.

Figure 6A:
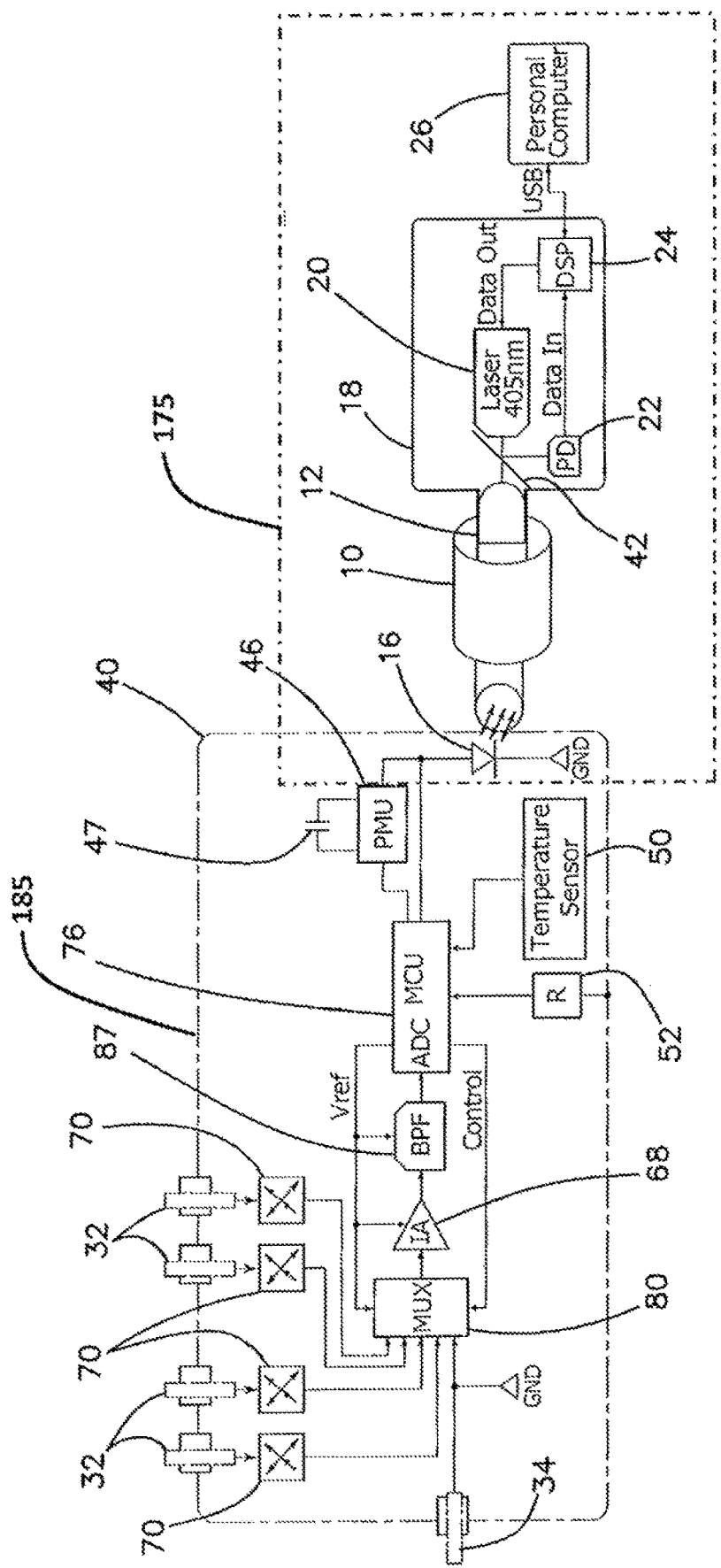
FIG. 6A is a block diagram of the embodiments whereby photonic power and data transmitted optically employing an Indium Gallium Nitride (InGaN) bidirectional LED.

FIG. 6A is a block diagram of yet another embodiment of the components in the catheter tip of FIG. 1 in which MUX 80 is coupled to tip ground electrode 34 and through a plurality of ESD circuits 70 to a corresponding plurality of MOSFET electrodes 32. IA 68 and bandpass filter 87 are then serially coupled between MUX 80 and the built-in ADC within MCU 76. MCU 76 generates a control signal to MUX 80 which controls the sequencing of the multiplexed data input signals from MOSFET electrodes 32. Temperature sensor 50 in turn is coupled to MCU 76 as is resistor 52. The catheter system 38 of FIG. 6A is fabricated in one embodiment as shown in FIG. 7, similar to the embodiment of FIG. 3. In the embodiment as depicted in FIG. 7, IA 68, BPF 87, and MCU 76 are mounted on and coupled to the top surface of FPCB 74 as top components 88 with MUX 80, capacitor 47 and module 46 are mounted on and coupled to the bottom surface of FPCB 74 as bottom components 90. LED/PD 16 and lens 72 are adjacent to and midline with FPCB 74 with optical fiber 12. As shown in the perpendicular cross sectional view of FIG. 8, as seen through section lines 8-8 of FIG. 7, top components 88 and bottom components 90 again present a stacking height with FPCB 74 of 2 mm or less with a width defined by the width of FPCB 74, which can be selected as 2.5 mm or less. FPCB is electrically coupled by wiring to catheter 40 for grounding purposes, FIG. 6A is a block diagram of the embodiments whereby photonic power and data transmitted optically employing an Indium Gallium Nitride (InGaN) bidirectional LED. FIG. 6A further shows the two sections of the catheter 40 whereby the catheter is schematically divided into a proximal section 175 represented by the handle 82 on FIG. 4 and a distal section of the catheter 185 containing the electrodes and the photonic machinery forming the bio sensing portion of the catheter.

Figure 6B:
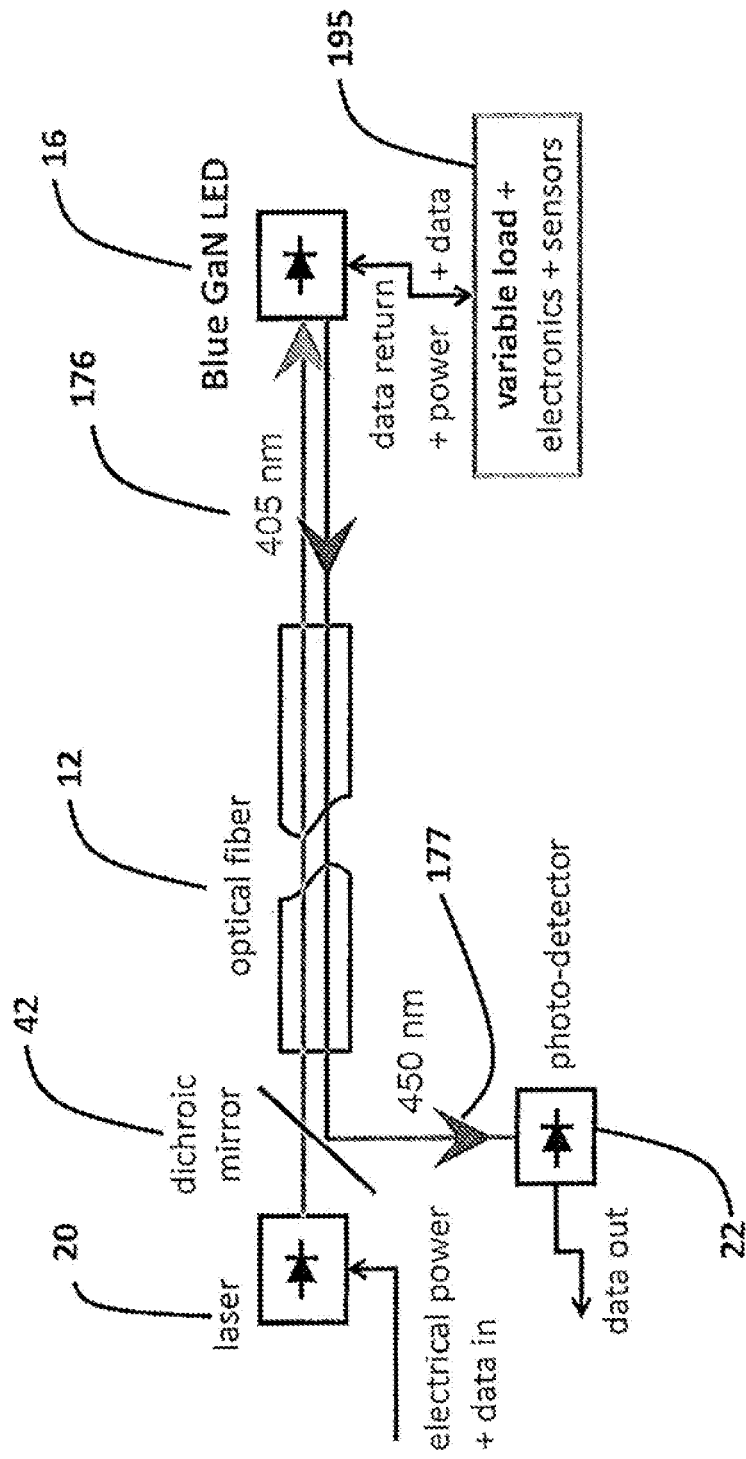
FIG. 6B is a schematic representation of the principle of operation of the photodiode and the laser forming the photonic scheme employed by the catheter for the detection of the biopotential.

FIG. 6B is a schematic representation of the principle of operation of the photodiode and the laser forming the photonic scheme employed by the catheter for the detection of the biopotential. The schematic forming the circuit of photonic power to the electronics where the laser 20 provides coherent light 176 (405 nm) through the dichroic mirror 42 and the optical fiber 12 to the LED/PD 16. The LED/PD 16 also selectively generates an optical signal 177 (450 nm) that returns through the optical fiber 12 to the dichroic mirror 42 where t is reflected to a photodiode 22. Further circuit 195 included in MCU 76 is a variable load which enables modulation of the signal formed by the blue InGaN LED/PD 16 to generate a data stream representing the biopotential detected by the electrodes 32. The operation of the laser 20 and the blue InGaN LED/PD 16 where DC power 176 (405 nm) is delivered to the catheter and where a return of a binary data stream to circuit 195 is further described by FIG. 6C.

Figure 6C:
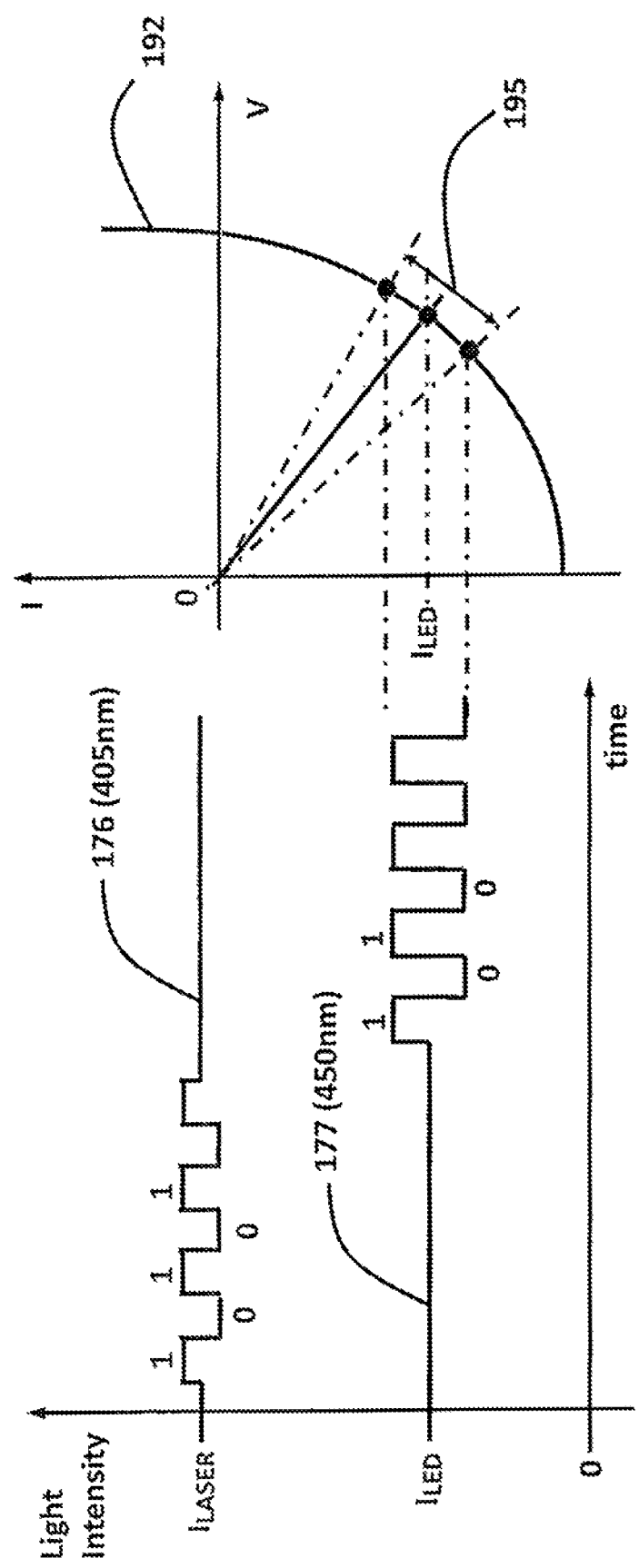
FIG. 6C is a pair of graphs illustrating how an LED and a laser forming the photonic detection and power mechanism are employed in the detection and data transmission of biopotential measurement employing a catheter. The graph in the left portion of the figure is a graph of the laser and LED intensity as a function of time. The graph in the right portion of the figure is a graph of the LED intensity as a function of applied voltage.

FIG. 6C is a pair of graphs illustrating how an LED and a laser forming the photonic detection and power mechanism are employed in the detection and data transmission of biopotential measurement employing a catheter. The graph in the left portion of the figure is a representation of the laser and LED intensity as a function of time. The graph in the right portion of the figure is a representation of the LED current as a function of applied voltage.

FIG. 6C indicate two modes of operation in the photonic scheme which enables the bio-detection of potentials within biological tissue. Whereby Laser 20 shown in FIG. 6B generates a light beam transmitted through a dichroic mirror 42 and optical fiber 12 so that a continuous light source power signal 176 with a wave length of 405 nm is delivered the through LED/PD 16 to power the electronics of ASIC 86. When reverse biased LED/PD 16 is generated by the variable load condition 195 and set by microcontroller 76, the equivalent voltage potential measured at the biological species (Heart surface tissue or nerve ending) a data stream 177 with a wave length of 450 nm, is emitted by employing the modulation of circuit 195 (photonic equivalent emission of the potential measured at the biological site), whereby a variable load, changes the intensity of the of light generated by LED/PD 16 to send a binary data stream. The use of bidirectional InGaN LED/PD 16 is possible by the employment of dichroic mirror 42 which splits the beam as well as the incorporation of a variable load which modulates the light intensity output by LED/PD 16. Clocked pulsed power is delivered at 405 nm and clocked binary data is returned at 450 nm as shown the left portion of FIG. 6C in a time-multiplexed fashion. The right portion of FIG. 6C graphically represents the relationship between the current/voltage curve 192 of LED/PD 16 and the variable load of circuit 195 to provide the binary states as represented in the left portion of FIG. 6C.

Figure 4:
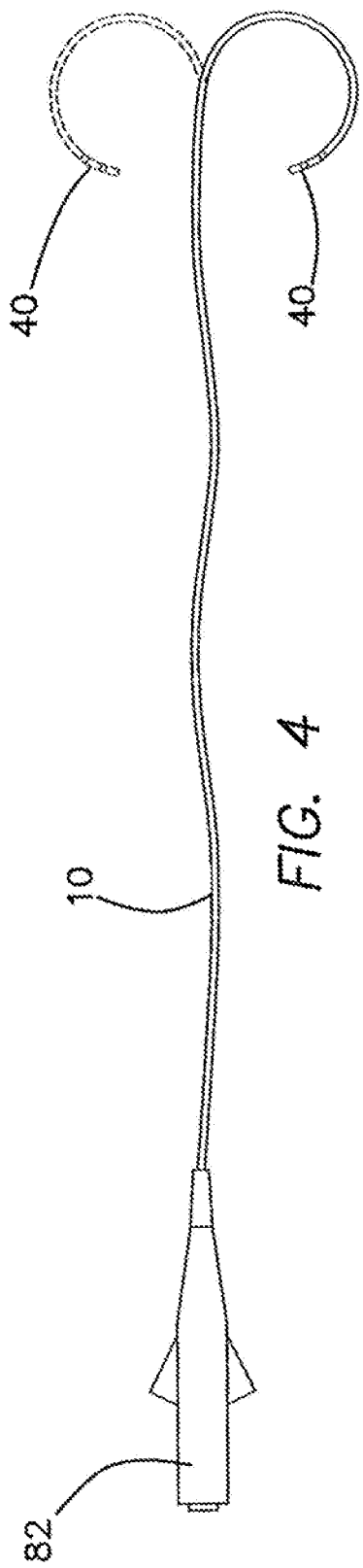
FIG. 4 is a side view of an assembled catheter system with a steerable tip.

FIG. 4 is a side view of an assembled catheter system with a steerable tip, A catheter handle 82 includes optical interface 18. Catheter cable 10 extends from handle 82 to the site of operation and terminates in catheter 40. A conventional stylet is included in catheter cable 10 and is controlled from handle 82 for steering and maneuvering the location of the catheter distal end, thereby enabling contact with the targeted site within the confinement of the biological species desired, e.g. heart surface tissue or nerve ending and, optionally catheter 40, to allow catheter 40 to be remotely steered from handle 82.

Figure 9:
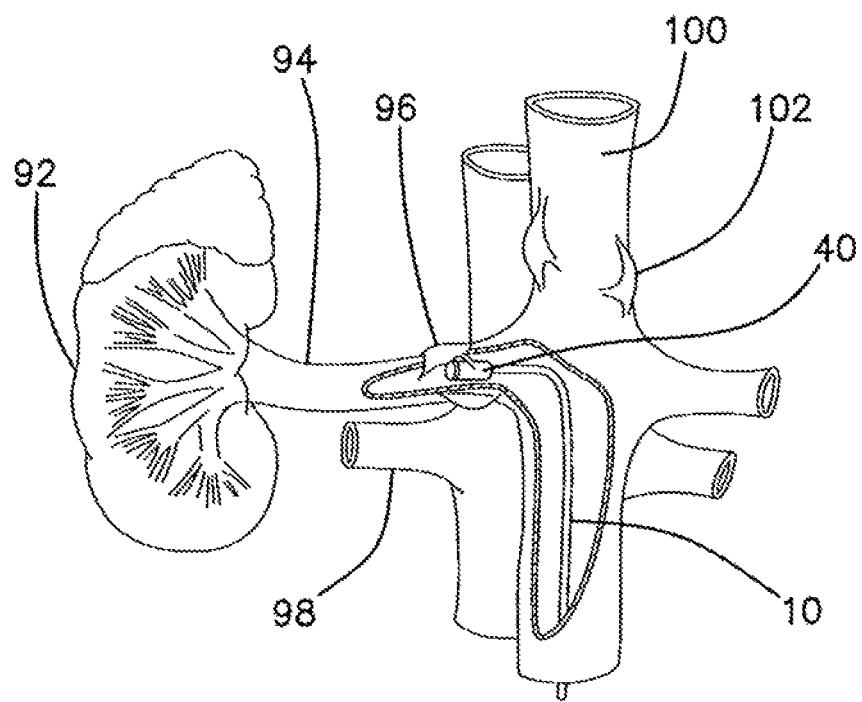
FIG. 9 is a diagram of the deployment of the catheter into the right renal tract for renal denervation using local amplification of biopotentials.

FIG. 9 illustrate a possible application of employing the invention within the current art of electrophysiological studies. The figure illustrates the deployment of the catheter 40 into the right renal arterial tract, adjacent to renal vein 98, for renal denervation (RDN), a minimally invasive procedure to treat resistant hypertension. The procedure uses radiofrequency ablation to burn the nerves in the renal arteries. This process causes a reduction in the nerve activity, which decreases blood pressure. The RDN protocol require a site-specific identification of renal artery 94, renal ganglion 96, and the electroanatomic location of arborized sympathetic renal nerve endings 104, the nerve 106 is then ablated by the use of radiofrequency modality through the adventitia 114, while correcting or modifying using local amplification of biopotentials sensed in the renal artery 94 of the left kidney 92. Catheter 40 is disposed through abdominal aorta 100 carrying aorto-corneal ganglion 102 into renal artery 94 in the proximity of renal ganglion 96. The use of the inventive device catheter 40 enable a proper definition of the location of the nerve ending and thereby will improve the diagnostic value of the current art of RDN.

Figure 10A:
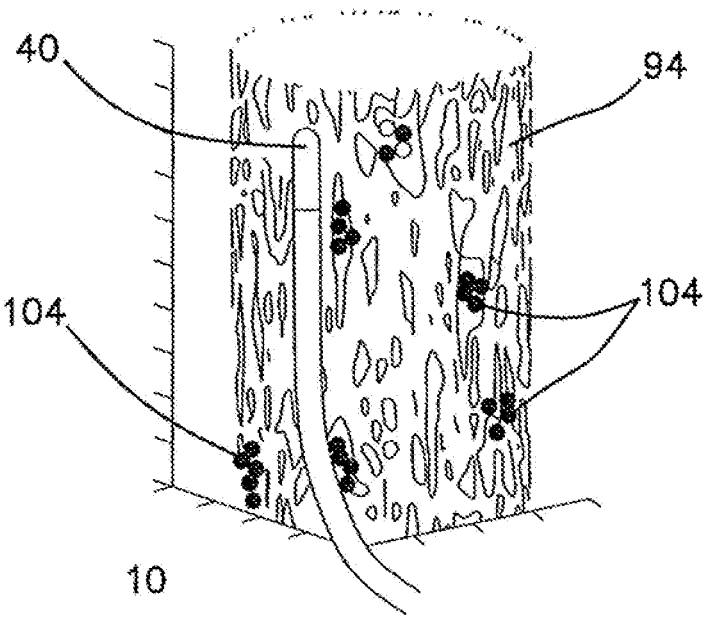
FIG. 10a is perspective diagram illustrating the renal detail of the renal artery of FIG. 9.

FIG. 10a is perspective diagram illustrating the renal detail of the renal artery of FIG. 9 in relation to the tip of catheter 40 and the fact that the anatomical variability of the arborized sympathetic renal nerve endings 104 is human specific and cannot be assumed to be a generic map, most of RDN procedure fail. See Hitesh C Patel et al. "Renal denervation for the management of resistant hypertension", Integr Blood Press Control. 2015; 8: 57-69, published online 2015 Dec. 3, doi: 10.2147/IBPC.S65632. FIG. 10a is an illustration of a left kidney 92 where the nerves innervating the kidneys are either efferent or afferent nerves. The nerves innervating the kidneys are either efferent or afferent nerves 106 shown in FIG. 10c. The efferent nerves derive from the neuraxins, along the renal artery 94 and vein. The afferent renal nerves travel from the kidney toward the dorsal root ganglia 96 along the spinal cord. The efferent renal nerves are postganglionic, and the majority of these are adrenergic, i.e., they contain norepinephrine varicosities at their nerve terminals.

An important neurotransmitter role for norepinephrine is supported by the observations that decreasing renal sympathetic nerve activity to zero by chronic renal denervation reduced renal tissue norepinephrine concentration by >95%, conversely, increasing renal sympathetic nerve activity by renal sympathetic nerve stimulation increased norepinephrine concentration in renal venous blood. The signal characteristics of the efferent or the afferent nerves 106 is identified by the low noise high sampling rate ADC 56, DSP 48 and PMU 46 in FIG. 5 forming a digital "snap shot" associated by the employment of the electronic scheme 164 and nerve ending-signal signature representation.

Figure 11:
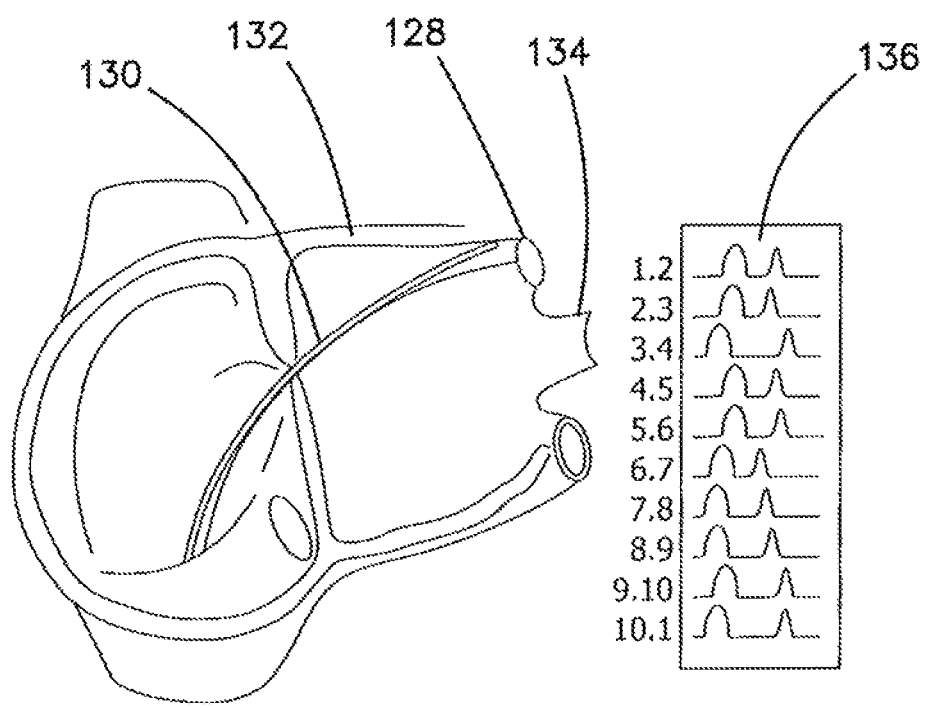
FIG. 11 is a diagram of a quadripolar and decapolar sensing catheter of the illustrated embodiments as disposed in the left ventricle of the heart.
Figure 10B:
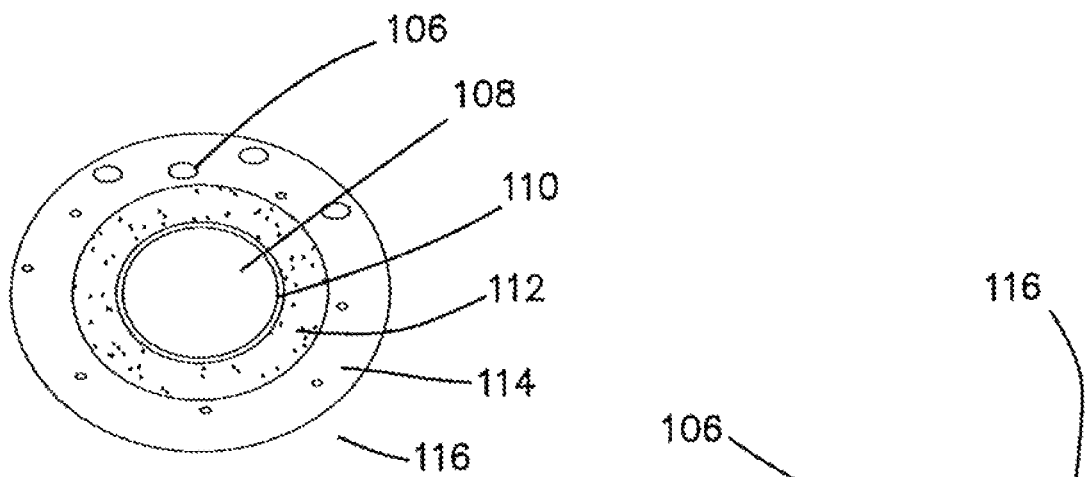
Figure 10C:
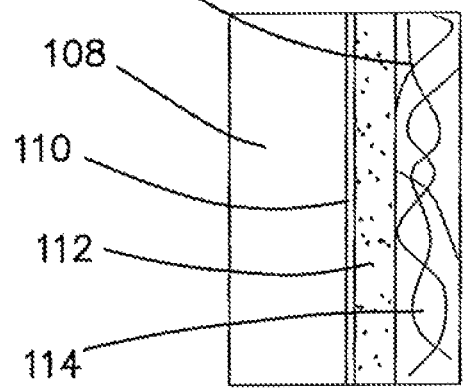
FIG. 10c is a longitudinal cross-sectional view the renal artery of FIGS. 10a and 10b.

The example of electro-anatomic cases, be it RDN in FIG. 9, electrophysiological study for arrythmia indicated by schematic FIG. 11, or nerve ending variable anatomical placement of efferent or the afferent nerves shown in FIGS. 10A, 10B and 10C are further illustrations of the needs for accurate mapping of electro-anatomical features where a proper diagnosis and spatial definition including a clear representation of the morphological characteristics of the signal(s) provides an important diagnostic information which in turn impact the therapeutic success of the medical interventional procedure i.e. RDN or EP study of arrythmias. FIG. 10a further illustrates the incorporation of apparatus for facilitating guided delivery of a MOSFET mapping (and potentially), delivering RF energy for ablation via catheter 40 to innervated tissue and ganglia that contribute to renal sympathetic nerve activity in accordance with embodiments of the invention.

In another embodiment, the RF ablation catheter 40 is used cooperatively with an imaging system such as known the art for example, an impedance mapping apparatus by such as the St. Jude Medical ENSITE or magnetic localization system, as exemplified as CARTO by J&J BioSense Webster, which enables a catheter to locate target within anatomical context and by provide geometric coordinates of specific anatomical destination e.g. renal nerves. This process of defining an anatomical site such as a renal plexus ganglion to effect a change of nerve signal or generally enhance a procedure, we generally classify as neuromodulation or a renal denervation. Specifically, where a surgical and/or electrical intervention deactivates the ability of the sympathetic nerve or its ganglia to influence the activity of the sympathetic autonomic nervous system to achieve a clinical outcome.

In another embodiment of the invention e improve the desired clinical outcome by employing the MOSFET sensor array of electrodes 32 within the catheter 40 in a stable position whereby the MOSFET sensor array of electrodes 32 registers a high bioelectrical potential and when an impedance sensor, which is software defined within the catheters digital circuitry, indicates a contact with a specific impedance value, the catheter 40 is than activated to deliver energy with a set value of e.g. 8-40 watts of RF energy. FIG. 10*a* describes a MOSFET sensor array of electrodes 32 and its irrigated RF ablation catheter 40 configured for maintaining the catheter in a stable position and orientation as detailed using the embodiments noted by the referenced patent noted above and by delivering the necessary energy to denervate the active site. The system and its methods provide the operator with the means to affect the modulation of nerve activity and achieve the desired goal of neuro-attenuation to achieve an optimal clinical goal.

The process described is governed by the use of the apparatus' ability to first provide an indication of position and orientation of the catheter 40 with constant impedance value indicating surface contact with the vessel lumen so as to be enable to deliver the necessary RF energy through the adventitia and where the ablating energy is transmitted to the renal nerve and the ganglia in an optimal and safe mode.

According to one embodiment, the irrigated ablation catheter 40 with its integrated MOSFET sensor array of electrodes 32 is delivered to a location within a patient's renal artery 94. The MOSFET sensor array catheter 40 preferably includes a mapping device, (not shown) such as EnSite Navix of St. Jude Medical or other mapping device such as CARTO produced by J&J BioSense Webster.

FIG. 10*b* is a perpendicular cross sectional view of the renal artery of FIG. 10*a* and FIG. 10*c* is a longitudinal cross sectional view of the renal artery of FIGS. 10*a* and 10*b*, which illustrate the structure of renal artery 94, namely showing the nerves 106 in the renal wall, the renal lumen 108, the endothelium 110 providing the lining of renal artery 94, the media layer 112 backing the endothelium 110, the surrounding adventitia 114 and finally the encasing fat tissues 116. The above anatomical details are an illustration of the complexity and variability of the anatomical sits, where biopotential activities must be distinguished, identified and recorded with fidelity so as to enable a therapeutic optimal result. This is the mainstay of the utility of the inventive steps of employing a local amplification and digitizing such distinct signal with fidelity and ohmic value that the current art can't deliver, due to the inherent signal-to-noise ratio (SNR) in the current architecture of electrodes processed at a distance.

FIG. 11 is a diagrammatic longitudinal side cross section of the left atrium of the heart 150 and where an electrophysiological study employing an optical catheter 40 combined with a decapolar catheter 128 to identify electrical potential biosignals 136 within the left superior pulmonary vein 148. With the use of the novel optical catheter, the SNR and far-field/near-field averaging customarily used by the current art is reduced substantially by recording the biopotential on the sites without averaging the signal and the fact that the native signal is digitized within the distal end of the catheter 128, the measured output cannot be corrupted by any external noise and/or pickup by the long shaft of the catheter. FIG. 11 illustrates the sensing of an excitable cellular matrix typical for heart's muscle. The sensed biosignals 136 from the decapolar catheter 128 are depicted in graphic form to illustrate an electrophysiological study, where a physical placement of multiple catheters in the left atrium to sense and afterward ablate the desired site(s) in order to correct an arrythmia, (e.g. such as Afib). The figure illustrates the case where multiple electrodes catheter 130 will display different biopotentials and unless we distinguish them and record them locally, the current art technology averages their values and can't distinguish between far and near field results.

Additionally, FIG. 11 is a graphical representation of a ganglionic waveform indicating the ability to distinguish characteristic waves. The use of the preferred embodiment in this application, with the ability to locally measure, amplify and record digitally the signal, is the mainstay of this application. The use of optical power and transmission of the digital data in a binary form further eliminates the needs to generate an averaging of the various electrodes, as the local signal may indicate a "non-standard" behavior which is the underlying representation of a disease. The conventional prior art employs electrodes, which inherently must average the signal over a timespan, and thereby reduce the resolution on a local level.

FIG. 11 is additionally an example of the embodiment of the invention where we use a graphic representation of ganglionic plexus signal and where the analogue complex wave is preserved by the machinery described above as it demonstrates the use of the catheter sensing capabilities and enables a consistent and measurable application of contact force as a function of impedance value to distinguish between the contact force over the tissue measured and the anatomical structure, and by further providing a safe and optimal contact force between the catheter distal end and the biological site or structure. This measure of force is essential for the fidelity of the measurement of the site, as nerve activity is subject to the physical inverse law. Hence the operator needs to know that the biopotential of the site in question is a measure of a bioelectric potential of near field from the contacted tissue as opposed to far fields carried by the blood flow transfusing through the renal artery.

Figure 12A:
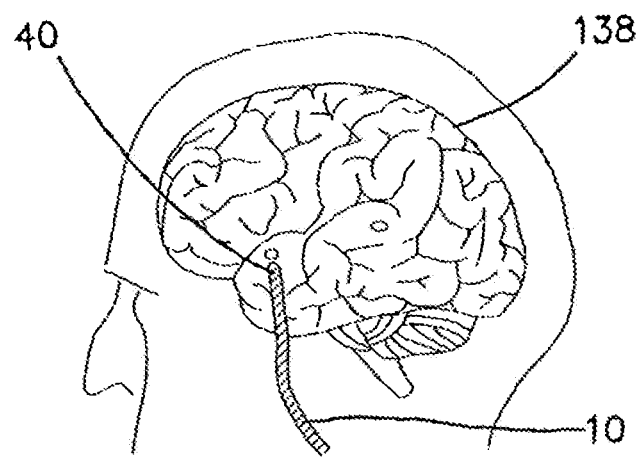
FIG. 12a is a diagram illustrating the use of the catheter to identify a focal epileptic origin in the brain.
Figure 12B:
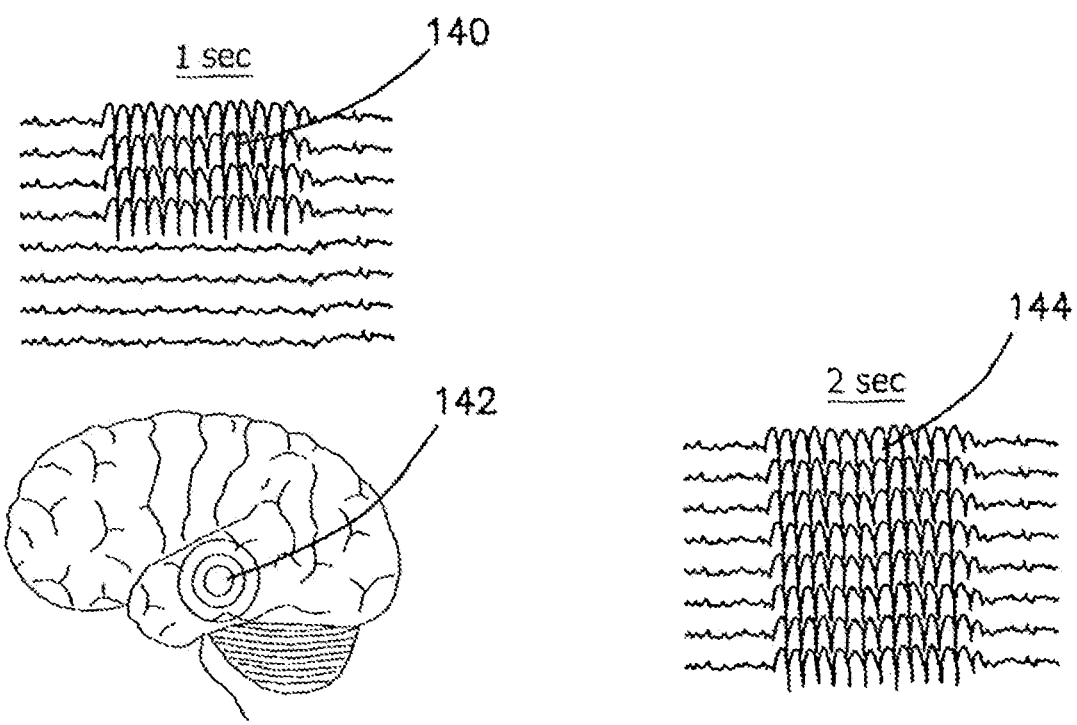
FIG. 12b is a diagram which in its upper portion illustrates the sensed biopotentials of a partial epileptic seizure and use of the catheter to identify a focal epileptic origin in the brain.
Figure 12C:
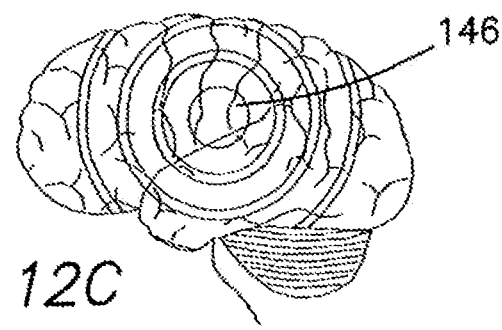
FIG. 12c is a diagram which in its upper portion illustrates the sensed biopotentials of a generalized epileptic seizure and use of the catheter to identify a focal epileptic origin in both sides of the brain.

FIGS. 12*a*-12*c* are side cross sectional views of a patient's brain 138 and optical catheter 40 whereby an electroanatomic study of focal epilepsies and seizures that emanate from an epileptogenic focus within the brain. FIG. 12*a* is a diagram illustrating the use of the catheter 40 to identify a focal epileptic origin in the brain 138. FIG. 12*b* is a diagram which in its upper portion illustrates the sensed biopotentials 140 of a partial epileptic seizure and use of the catheter 40 to identify a focal partial seizure epileptic origin 142 in the brain 138. FIG. 12*b* indicates a clinical representation of a local seizure 142 identified by the corresponding electroencephalogram noted by the waveforms of the local seizure signals 144, which indicates the seizure epicenter. FIG. 12*c* is a diagram which in its upper portion illustrates the sensed biopotentials 144 of a generalized epileptic seizure and use of the catheter 40 to identify a generalized focal epileptic origin 146 in both sides of the brain, FIG. 12*c* further elaborates on the ability of a precise biopotential catheter of the type described by this invention which enables the distinction of such an apparatus to discriminate between localized seizures verses global seizures 146. The corresponding electroencephalogram 144 represents the various electrode of the existing arts of measuring brain output while the catheter 40 identifies the anatomical and topographical localization of the epicenter.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are disclosed in above even when not initially claimed in such combinations. A teaching that two elements are combined in a claimed combination is further to be understood as also allowing for a claimed combination in which the two elements are not combined with each other but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and what essentially incorporates the essential idea of the embodiments.

We claim:

1. An apparatus used in combination with a computer for sensing biopotentials comprising:
 a catheter comprising:
  a plurality of sensing electrodes;
  a corresponding plurality of local amplifiers, each coupled to one of the plurality of sensing electrodes;
  a data, control and power circuit coupled to the plurality of local amplifiers;
  a photonic device bidirectionally communicating an electrical signal with the data, control and power circuit and communicating an optical signal with an optical fiber,
  wherein the photonic device bidirectionally communicates the optical signal with the optical fiber; and
 a flexible printed circuit board and wherein the local amplifiers and data, control and power circuit comprise application specific integrated circuits (ASICs) mounted on both sides of the flexible printed circuit board within the catheter having a size of 11 French or smaller; and
 an optical interface device to provide optical power to the optical fiber and thence to the photonic device and to receive optical signals through the optical fiber from the photonic device, wherein the optical interface device bidirectionally communicates an electrical data, control and power signal to the computer.

2. The apparatus of claim 1 wherein the optical interface device includes a laser to provide optical power to the optical fiber.

3. The apparatus of claim 2 wherein the optical interface device includes a photodetector to receive optical signals through the optical fiber from the photonic device.

4. The apparatus of claim 3 wherein the optical interface device includes a digital signal processor to control and communicate with the laser and photodiode, and to communicate with the computer.

5. The apparatus of claim 1 wherein the optical interface device includes a photodetector to receive optical signals through the optical fiber from the photonic device.

6. The apparatus of claim 1 further comprising a catheter cable coupling the optical interface device and the catheter, wherein the optical fiber is included in the catheter cable, which is MRI compatible and EMI impervious.

7. The apparatus of claim 6 wherein only optical signals are communicated within the catheter cable.

8. The apparatus of claim 1 wherein the plurality of electrodes each comprise a MOSFET electrode.

9. The apparatus of claim 1 further comprising a flexible printed circuit board and wherein the local amplifiers and data, control and power circuit comprise application specific integrated circuits (ASICs) mounted on both sides of the flexible printed circuit board having a width of 2.5 mm or less and a height including the ASICs of 2 mm or less.

10. The apparatus of claim 1 wherein the photonic device selectively operates as both a light emitting diode or a photodiode depending on bias control.

11. The apparatus of claim 1 wherein the data, control and power circuit includes a multiplexer coupled to the plurality of electrodes.

12. The apparatus of claim 1 wherein the plurality of local amplifiers each have programmable gain.

13. The apparatus of claim 1 wherein the plurality of electrodes sense analog electrical biopotentials and where the data, control and power circuit includes an analog to digital converter to process the electrical biopotentials in digital form and wherein the photonic device communicates the electrical digital biopotential through the optical fiber to the optical interface as optical digital biopotential signals.

14. The apparatus of claim 1 wherein the catheter is configured as an electrophysiology catheter, renal denervation catheter, neuromodulation catheter, or an epileptic brain catheter.

15. The apparatus of claim 1 further comprising a temperature sensor coupled to the data, control and power circuit.

* * * * *